United States Patent [19]
Grofmeyer et al.

[11] Patent Number: 6,004,585
[45] Date of Patent: Dec. 21, 1999

[54] GRANULAR COMPOSITION OF A TRIAZINE COMPOUND

[75] Inventors: Dorothea Grofmeyer, Langenfeld; Christian Mundt, Erkrath; Christian Wegner, Köln, all of Germany

[73] Assignee: Bayer Aktiengesellschaft, Leverkusen, Germany

[21] Appl. No.: 09/117,550

[22] PCT Filed: Jan. 23, 1997

[86] PCT No.: PCT/EP97/00310

§ 371 Date: Jul. 31, 1998

§ 102(e) Date: Jul. 31, 1998

[87] PCT Pub. No.: WO97/28804

PCT Pub. Date: Aug. 14, 1997

[30] Foreign Application Priority Data

Feb. 5, 1996 [DE] Germany .................... 196 03 984

[51] Int. Cl.$^6$ .................... A61K 31/53; A61K 9/14
[52] U.S. Cl. .................... 424/499; 424/501; 424/502; 424/489; 424/438; 424/442; 514/241; 514/246; 514/951

[58] Field of Search .................... 514/951, 241, 514/246; 424/489, 493, 438, 442, 498, 499, 501, 502

[56] References Cited

U.S. PATENT DOCUMENTS

| | | |
|---|---|---|
| 4,826,842 | 5/1989 | Mehlhorn et al. . |
| 5,629,312 | 5/1997 | Bousseau et al. . |
| 5,866,597 | 2/1999 | Baxter . |

FOREIGN PATENT DOCUMENTS

| | | |
|---|---|---|
| 94 21260 | 9/1994 | WIPO . |
| 94/20108 | 9/1994 | WIPO . |
| 94/21260 | 9/1994 | WIPO . |
| 96 17611 | 6/1996 | WIPO . |

*Primary Examiner*—Thurman K. Page
*Assistant Examiner*—Brian K. Seidleck
*Attorney, Agent, or Firm*—Joseph C. Gil; Godfried R. Akorli

[57] ABSTRACT

The present invention relates to dust free, easily flowable and dosable granular compositions containing triazine, having a particle size distribution of between 40 and 400$\mu$ and an upper limit of particle size at 2000$\mu$, which can be effectively mixed with feed for administration to animals.

2 Claims, No Drawings

GRANULAR COMPOSITION OF A TRIAZINE COMPOUND

This application is a 371 of PCT/EP97/00310, filed Jan. 23, 1997.

The present invention relates to triazine granules and their preparation.

Toltrazuril (1-methyl-3-(3-methyl-4-(4-(trifluoromethyl) thio)phenoxy)phenyl)-1,3,5-triazine-2,4,6(1H, 3H, 5H)trione) is a known active compound against coccidia. It is customarily used in the form of aqueous solutions or suspensions. For many application areas, the solutions can only be employed with difficulty.

The present invention relates to triazine granules of the following composition a) active compound 0.5 to 10% (weight)
b) starch 10 to 40% (weight)
c) lactose 30 to 60% (weight)
d) polyvinylpyrrolidone 5 to 35% (weight)

having an average particle size distribution of between 40 to 400 $\mu$ and an upper limit of the particle size of 2000$\mu$.

The granules are prepared by premixing the components a) to d) in a suitable mixing or stirring vessel and spraying with a solution of polyvinylpyrrolidone. The granules are subsequently dried and, if necessary, screened off.

Dust-free, dry, easily flowing and easily dosable granules are obtained. These granules are preferably employed for the treatment of coccidiosis disorders of cats and other domestic animals and pets. Besides cats, the domestic animals and pets include dogs, rabbits and ornamental birds.

The granules are administered by mixing with solid, semi-solid or liquid feed. According to experience, feed which has been treated with the granules according to the invention is absorbed without problems even by sensitive animals.

Active compounds which may be mentioned are symmetrical 1,3,5-triazine-2,4,6(1H, 3H, 5H)-triones such as toltrazuril, unsymmetrical 1,2,4-triazine-3,5-diones such as diclazuril (2,6-dichloro-α-(4-chlorophenyl)-4-(4,5-dihydro-3,5-dioxo-1,2,4-triazin-2(3H)-yl)-phenylacetonitrile).

Toltrazuril may be preferably mentioned. The active compounds are employed at 0.5 to 10, preferably 1 to 5, particularly preferably 2 to 4% by weight.

Starches which may be mentioned are the customary types of starch such as potato starch, maize starch, cereal starch. Maize starch may preferably be mentioned. Starch is employed at 10 to 40, preferably 20 to 30, particularly preferably about 25% by weight.

Lactose is employed as a monohydrate in concentrations of from 30 to 60, preferably 50 to 60, particularly preferably about 60% by weight.

Polyvinylpyrrolidone (PVP) is preferably employed as an average molecular weight PVP having a K value of 24 to 32. PVP having a K value of 24 to 30, particularly preferably 25, is particularly preferred. The solvent employed for PVP is preferably water. Solvents which may also be mentioned are organic solvents on their own or as a mixture with water.

A K value of 25 corresponds to a weight average of the molecular mass of 28000 to 34000. The K value characterizes the average molecular mass.

PVP is preferably employed in a total amount of from 10 to 30% by weight.

The particle size distribution is between 40 to 400$\mu$, preferably between 80 and 200$\mu$, with an upper limit at 2000$\mu$, preferably at 1000$\mu$.

The granules according to the invention are prepared in solid mixers, preferably in fluidized bed granulators.

For the preparation, the individual components are homogeneously mixed at room temperature. The mixture is then sprayed with a 10 to 50% strength, preferably 30 to 40% strength, particularly preferably a 30% strength, aqueous PVP solution and optionally sprayed with further water. Per kg of mixture, 100 to 300, preferably 150 to 200 ml, of spray solution are employed. Granulation is carried out at 20 to 50° C., preferably at 25 to 40° C.

The granules are then dried at about 40 to 70° C., preferably at 50 to 60° C.

EXAMPLE 1

Preparation:

1. 500 g of polyvinylpyrrolidone having a K value of 25=PVP-25 are introduced into 1250 g of water (demineralized) at room temperature in the course of 2 hours with stirring using a toothed disc stirrer. The mixture is stirred for 1 hour until dissolution is complete.
2. 2500 g of maize starch, 1000 g of PVP-25, 200 g of toltrazuril and 5800 g of lactose are initially introduced into a fluidized bed granulator of the Aeromatic S 2 type. The mixture is homogenized for 10 minutes in a fluidized bed with fluidization at 150 to 200 m$^3$/h and temperature control at 25 to 30° C.
3. The prewarming phase up to reaching 25 to 40° C. admitted air temperature should be 2 to 4 minutes.
4. In the fluidized bed granulator, the premixture is granulated at a spraying pressure of 2 bar with 35 to 40° C. admitted air, 22 to 30° C. waste air and an admitted air amount of 150 to 200 m$^3$/h with spraying of 30 g of spray solution/minute.

The PVP initial solution from Preparation 1 is sprayed.

For rinsing the nozzle, approximately 100 g of denat. water are added.

Drying is then carried out at 150–200 m$^3$/h with 55° C. admitted air to 42–45° C. waste air temperature.

5. In order to exclude any coarse granules or wall deposits possibly present, granules over 2000 $\mu$m are screened off.

We claim:

1. A granular composition comprising:
    a) a triazine compound 0.5 to 10% (weight)
    b) starch 10 to 40% (weight)
    c) lactose 30 to 60% (weight)
    d) polyvinylpyrrolidone 5 to 35% (weight) having an average particle size distribution of between 40 to 400$\mu$ and an upper limit of the particle size at 2000$\mu$.

2. A process for the preparation of a granular composition comprising:
    a) triazine compound 0.5 to 10% (weight)
    b) starch 10 to 40% (weight)
    c) lactose 30 to 60% (weight)
    d) polyvinylpyrrolidone 5 to 35% (weight)
with a particle size distribution of between 40 to 400$\mu$ and an upper limit of the particle size at 2000$\mu$, characterized in that the components a) to d) are premixed in a suitable mixing or stirring vessel and sprayed with a solution of polyvinylpyrrolidone, dried and optionally screened off.

* * * * *